(12) United States Patent
Kunkel et al.

(10) Patent No.: US 8,983,622 B2
(45) Date of Patent: Mar. 17, 2015

(54) IMPLANTABLE LEADS WITH OPTIMIZED LEAD BODY CROSS-SECTION CONFIGURATION

(75) Inventors: Ronald W. Kunkel, Jim Falls, WI (US); Andrew De Kock, Andover, MN (US); Steven B. Rasmussen, Forest Lake, MN (US); Patrick Willoughby, Hugo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 646 days.

(21) Appl. No.: 12/939,803

(22) Filed: Nov. 4, 2010

(65) Prior Publication Data

US 2011/0160819 A1 Jun. 30, 2011

Related U.S. Application Data

(60) Provisional application No. 61/291,110, filed on Dec. 30, 2009.

(51) Int. Cl.
*A61N 1/05* (2006.01)

(52) U.S. Cl.
CPC .............. *A61N 1/056* (2013.01); *A61N 1/0573* (2013.01)
USPC ............................ 607/116; 607/119; 607/122

(58) Field of Classification Search
USPC ........................... 607/2, 9, 116, 118, 119, 122
See application file for complete search history.

(56) References Cited

U.S. PATENT DOCUMENTS

| | | | |
|---|---|---|---|
| 5,303,704 | A | 4/1994 | Molacek et al. |
| 5,324,321 | A | 6/1994 | Pohndorf et al. |
| 5,584,873 | A | 12/1996 | Shoberg et al. |
| 5,619,993 | A | 4/1997 | Lee |
| 5,674,272 | A | 10/1997 | Bush et al. |
| 5,674,273 | A | 10/1997 | Helland |
| 5,826,576 | A | 10/1998 | West |
| 6,185,463 | B1 | 2/2001 | Baudino |
| 6,249,708 | B1 | 6/2001 | Nelson et al. |
| 6,400,992 | B1 | 6/2002 | Borgersen et al. |
| 6,434,430 | B2 | 8/2002 | Borgersen et al. |
| 6,501,991 | B1 * | 12/2002 | Honeck et al. ................ 607/122 |
| 6,718,211 | B2 | 4/2004 | Smits |
| 6,741,893 | B2 | 5/2004 | Smits |
| 7,289,846 | B2 | 10/2007 | Shoberg et al. |
| 7,395,116 | B2 | 7/2008 | Mehdizadeh et al. |

(Continued)

FOREIGN PATENT DOCUMENTS

| | | |
|---|---|---|
| CN | 1147964 A | 4/1997 |
| JP | 3118759 U | 12/1991 |
| JP | 2002100714 B2 | 8/2007 |

OTHER PUBLICATIONS

Active Implantable medical devices—Part 2-1: Particular requirements for active implantable medical devices intended to treat bradyarrhythmia (cardiac pacemakers), British Standard, BS EN 45502-2-1:2003, 98 pages.

(Continued)

*Primary Examiner* — Carl H Layno
*Assistant Examiner* — Pamela M Bays
(74) *Attorney, Agent, or Firm* — Fagre Baker Daniels LLP

(57) ABSTRACT

Medical lead body configurations that reduce conductor flexural fatigue. The various lead body embodiments include a support section and can also include other features such as a semi-straight portion of a lumen or semi-straight sides that optimize the reduction in conductor flexural fatigue.

20 Claims, 9 Drawing Sheets

(56) References Cited

U.S. PATENT DOCUMENTS

| | | |
|---|---|---|
| 7,500,949 B2 | 3/2009 | Gottlieb et al. |
| 2002/0065544 A1 | 5/2002 | Smits |
| 2006/0089695 A1* | 4/2006 | Bolea et al. .................. 607/122 |
| 2008/0046059 A1 | 2/2008 | Zarembo et al. |
| 2009/0203258 A1 | 8/2009 | Guenther et al. |
| 2009/0210044 A1* | 8/2009 | Reddy et al. .................. 607/127 |
| 2009/0248126 A1 | 10/2009 | Nippoldt et al. |

OTHER PUBLICATIONS

International Search Report and Written Opinion issued in PCT/US2010/059492, mailed Mar. 3, 2011, 12 pages.

Office Action issued in JP Application No. 2012-547098, Apr. 8, 2014, 6 pages (with English translation).

* cited by examiner

IMPLANTABLE LEADS WITH OPTIMIZED LEAD BODY CROSS-SECTION CONFIGURATION

CROSS-REFERENCE TO RELATED APPLICATION

This application claims priority under 35 U.S.C. §119 to U.S. Provisional Application No. 61/291,110, filed on Dec. 30, 2009, entitled "Implantable Leads with Optimized Lead Body Cross-Section," which is incorporated herein by reference in its entirety for all purposes.

TECHNICAL FIELD

The various embodiments disclosed herein relate to body implantable medical devices for sensing electrical impulses and/or delivering electrical stimulation in a body, and more particularly, to methods and devices relating to a lead body having an optimal configuration to reduce conductor flexural fatigue and/or failures.

BACKGROUND

Various types of medical electrical leads for use in cardiac rhythm management systems are known. Such leads are typically extended intravascularly to an implantation location within or on a patient's heart, and thereafter coupled to a pulse generator or other implantable device for sensing cardiac electrical activity, delivering therapeutic stimuli, and the like. The leads are desirably highly flexible to accommodate natural patient movement, yet also constructed to have minimized profiles. At the same time, the leads are exposed to various external forces imposed, for example, by the human muscular and skeletal system, the pulse generator, other leads, and surgical instruments used during implantation and explantation procedures. There is a continuing need for improved lead designs.

SUMMARY

Discussed herein are various lead body configurations for implantable medical electrical leads, including lead bodies having a support portion, as well as medical electrical leads including such lead bodies.

In Example 1, a medical lead comprises a lead body comprising a coil lumen defined within the lead body, at least two cable lumens defined within the lead body, and a support portion defined within the lead body and extending longitudinally within the lead body and disposed between the coil lumen and the cable lumens. The coil lumen extends from a proximal portion to a distal portion of the lead body. Each of the at least two cable lumens extends from the proximal portion to the distal portion. The support portion has a width extending from a first side of the lead body to a second side and a thickness configured to reduce flexural fatigue of a conductor disposed within the coil lumen or the cable lumens.

Example 2 relates to the medical lead according to Example 1, wherein the thickness comprises a minimum thickness that extends along the width of the support portion.

Example 3 relates to the medical lead according to either Example 1 or 2, wherein the minimum thickness is at least 2.24% of a total diameter of the lead body.

Example 4 relates to the medical lead according to any of Examples 1-3, wherein the minimum thickness is at least 0.0015 inches.

Example 5 relates to the medical lead according to any of Examples 1-4, wherein the coil lumen has an inner wall having a circumference, wherein the circumference has a semi-straight portion, wherein the semi-straight portion is substantially adjacent to the support portion and is substantially parallel with the width of the support portion, wherein the semi-straight portion is configured to further reduce the flexural fatigue.

Example 6 relates to the medical lead according to any of Examples 1-5, wherein each of the first and second sides of the lead body comprise a semi-straight side extending longitudinally along each of the first and second sides, wherein each of the semi-straight sides are configured to further reduce the flexural fatigue.

Example 7 relates to the medical lead according to any of Examples 1-6, wherein the coil lumen has a substantially elliptical cross-section, wherein the substantially elliptical cross-section is configured to further reduce the flexural fatigue.

Example 8 relates to the medical lead according to any of Examples 1-7, wherein at least a portion of the proximal portion comprises polyurethane.

In Example 9, a medical lead comprises a lead body having a cross-section, the cross-section comprising a coil lumen defined in the lead body, at least two cable lumens defined in the lead body, and a support portion defined in the lead body and disposed between the coil lumen and the at least two cable lumens. The coil lumen is configured to receive a coil conductor. Each of the at least two cable lumens are configured to receive a cable conductor. The support portion has a width extending from a first side of the cross-section to a second side and a thickness of at least 2.24% of a total diameter of the lead body, wherein the thickness is configured to reduce flexural fatigue of the coil conductor or the cable conductor.

Example 10 relates to the medical lead according to Example 9, wherein the coil lumen has an inner wall having a circumference, wherein the circumference has a semi-straight portion, wherein the semi-straight portion is substantially adjacent to the support portion and is substantially parallel with the width of the support portion, wherein the semi-straight portion is configured to further reduce the flexural fatigue.

Example 11 relates to the medical lead according to Example 9 or 10, wherein each of the first and second sides of the lead body comprise a semi-straight side extending longitudinally along each of the first and second sides, wherein each of the semi-straight sides are configured to further reduce the flexural fatigue.

Example 12 relates to the medical lead according to any of Examples 9-11, wherein the coil lumen has a substantially elliptical cross-section, wherein the substantially elliptical cross-section is configured to further reduce the flexural fatigue.

Example 13 relates to the medical lead according to any of Examples 9-12, wherein the thickness is at least 0.0015 inches.

In Example 14, a medical lead comprises a lead body, the lead body comprising a distal section, a proximal section, a coil lumen defined within the lead body and extending from a proximal portion to a distal portion of the lead body, at least two cable lumens defined within the lead body and extending from the proximal portion to the distal portion, and a support portion defined within the lead body and extending longitudinally within the lead body and disposed between the coil lumen and the at least two cable lumens. The distal section comprises a spiral configuration and at least one electrode. The proximal section comprises a terminal connector. The coil lumen has a substantially elliptical cross-section and is configured to receive a coiled conductor. The at least two cable lumens are each configured to receive a cable conductor, wherein the cable conductor is configured to couple one of the at least one electrodes to the terminal connector. The support portion has a width extending from a first side of the lead body to a second side and a thickness configured to reduce flexural fatigue of at least one of the cable conductor and the coiled conductor. The substantially elliptical cross-section of the coil lumen is configured to further reduce the flexural fatigue.

Example 15 relates to the medical lead according to Example 14, wherein the thickness comprises a minimum thickness that extends along the width of the support portion.

Example 16 relates to the medical lead according to Example 14 or 15, wherein the minimum thickness is at least 2.24% of a total diameter of the lead body.

Example 17 relates to the medical lead according to any of Examples 14-16, wherein the minimum thickness is at least 0.0015 inches.

Example 18 relates to the medical lead according to any of Examples 14-17, wherein the coil lumen has an inner wall having a circumference, wherein the circumference has a semi-straight portion, wherein the semi-straight portion is substantially adjacent to the support portion and is substantially parallel with the width of the support portion, wherein the semi-straight portion is configured to further reduce the flexural fatigue.

Example 19 relates to the medical lead according to any of Examples 14-18, wherein each of the first and second sides of the lead body comprise a semi-straight side extending longitudinally along each of the first and second sides, wherein each of the semi-straight sides are configured to further reduce the flexural fatigue.

Example 20 relates to the medical lead according to any of Examples 14-19, wherein at least a portion of the distal section comprises silicone and at least a portion of the proximal section comprises polyurethane.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
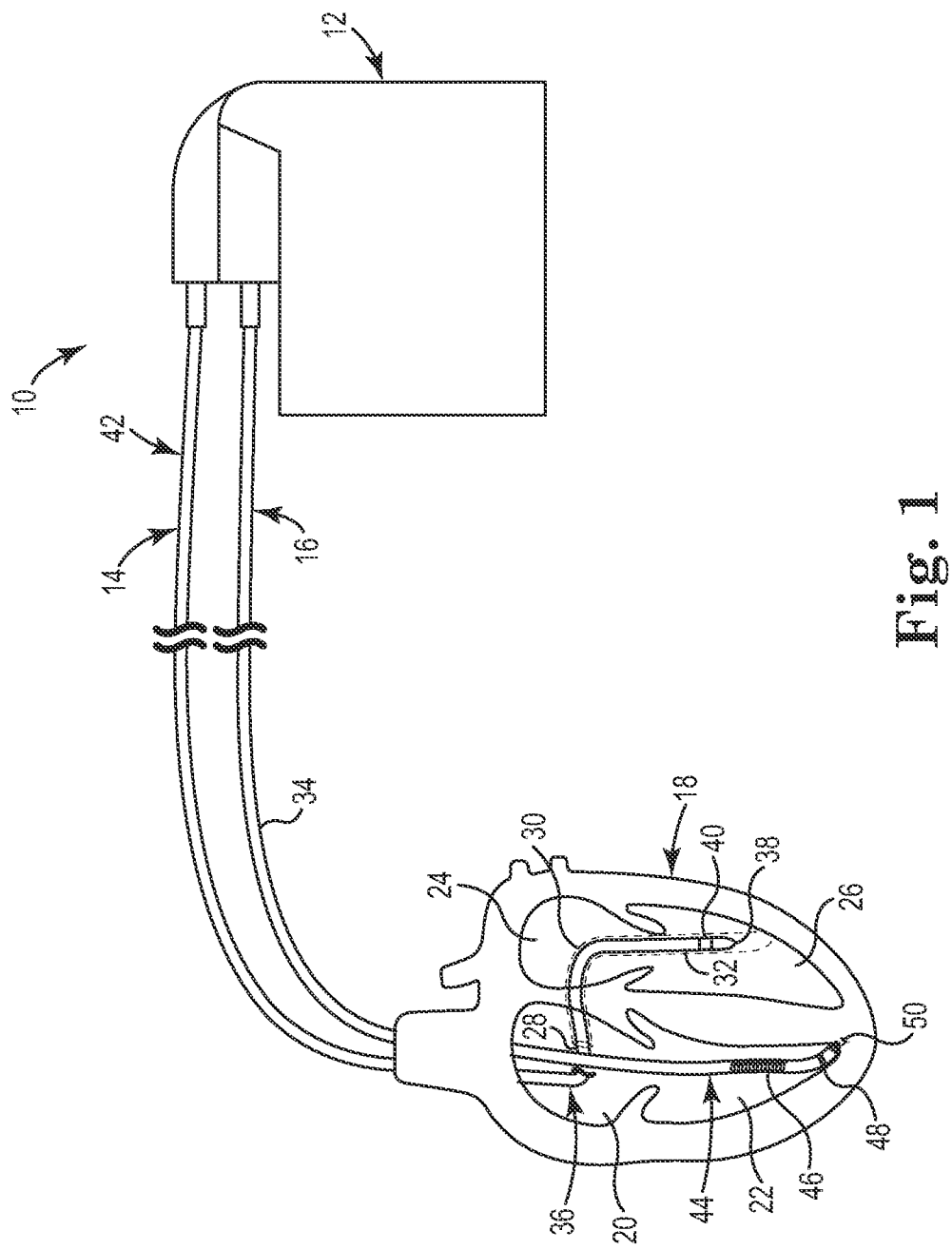
FIG. 1 is a schematic drawing of a cardiac rhythm management system including a pulse generator coupled to a pair of medical electrical leads deployed in a patient's heart, according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The various embodiments disclosed herein relate to various lead body configurations for use in a medical electrical lead. The leads according to the various embodiments of the present invention are suitable for sensing intrinsic electrical activity and/or applying therapeutic electrical stimuli to a patient. Exemplary applications include, without limitation, cardiac rhythm management (CRM) systems and neurostimulation systems. For example, in exemplary CRM systems utilizing pacemakers, implantable cardiac defibrillators, and/or cardiac resynchronization therapy (CRT) devices, the medical electrical leads according to embodiments of the invention can be endocardial leads configured to be partially implanted within one or more chambers of the heart so as to sense electrical activity of the heart and apply a therapeutic electrical stimulus to the cardiac tissue within the heart. Additionally, the leads formed according to embodiments of the present invention may be particularly suitable for placement in a coronary vein adjacent to the left side of the heart so as to facilitate bi-ventricular pacing in a CRT or CRT-D system. Still additionally, leads formed according to embodiments of the present invention may be configured to be secured to an exterior surface of the heart (i.e., as epicardial leads). FIG. 1 is a schematic drawing of a cardiac rhythm management system 10 including a pulse generator 12 coupled to a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

As shown in FIG. 1, lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes a distal end 38 and an electrode 40 both positioned within the branch vessel 32. The illustrated position of the lead 14 may be used for delivering a pacing and/or defibrillation stimulus to the left side of the heart 18. Additionally, it will be appreciated that the lead 14 may also be partially deployed in other regions of the coronary venous system, such as in the great cardiac vein or other branch vessels for providing therapy to the left side or right side of the heart 18.

In the figure, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. As will be appreciated, the high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

The lead 16 can include additional defibrillation/cardioversion and/or additional pace/sense electrodes positioned along the lead 16 so as to provide multi-polar defibrillation/cardioversion capabilities. In one example, the lead 16 includes a proximal high voltage electrode in addition to the electrode 46 positioned along the lead 16 such that it is located in the right atrium 20 (and/or superior vena cava) when implanted. As will be appreciated, additional electrode configurations can be utilized with the lead 16. In short, any electrode configuration can be employed in the lead 16 without departing from the intended scope of the present invention.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter defibrillator (ICD), a cardiac resynchronization (CRT) device configured for bi-ventricular pacing, and/or includes combinations of pacing, CRT, and defibrillation capabilities.

Figure 2:
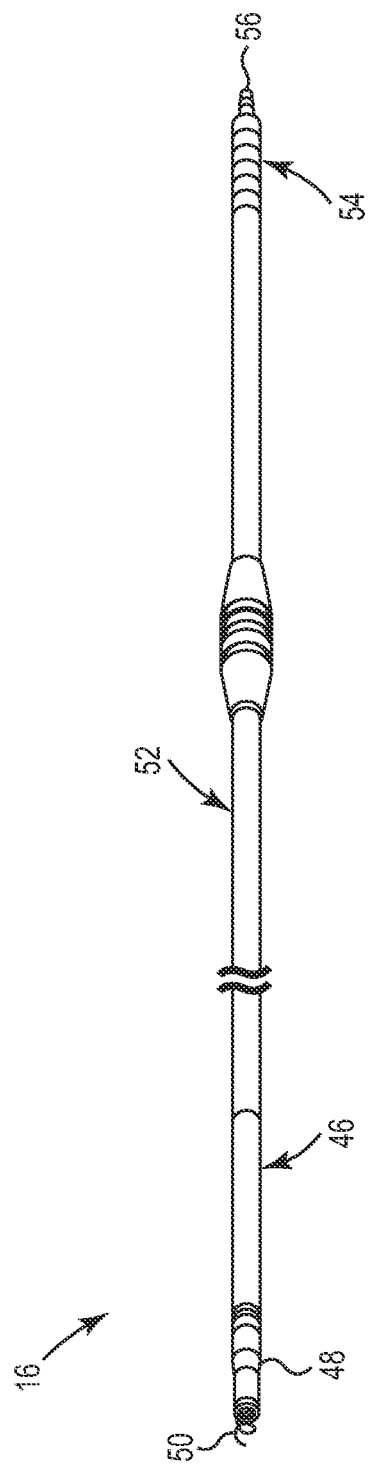
FIG. 2 is a perspective view of one of the leads shown in FIG. 1, according to one embodiment.

FIG. 2 is a perspective view of the lead 16 shown in FIG. 1. As discussed above, the lead 16 is adapted to deliver electrical pulses to stimulate a heart and/or for receiving electrical pulses to monitor the heart. The lead 16 includes an elongated polymeric lead body 52, which may be formed from any polymeric material such as polyurethane, polyamide, polycarbonate, silicone rubber, or any other known polymer for use in this type of lead.

As further shown, the lead 16 further includes a connector 54 operatively associated with the proximal end of the lead body 52. The connector 54 is configured to mechanically and electrically couple the lead 16 to the pulse generator 12 as shown in FIG. 1, and may be of any standard type, size or configuration. The connector 54 has a terminal pin 56 extending proximally from the connector 54. As will be appreciated, the connector 54 is electrically and mechanically connected to the electrodes 46, 48, 50 by way of one or more conductors (not shown) that are disposed within an elongate tubular member 58 within the lead body 52 (as best shown in cross-section in FIG. 3).

Figure 3:
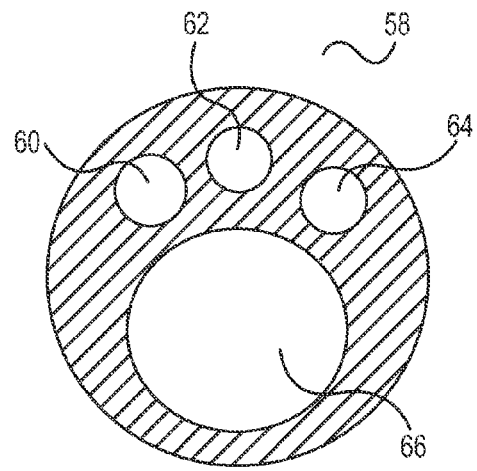
FIG. 3 is a schematic cross-section drawing of a portion of a lead, according to one embodiment.

The elongate tubular member 58 depicted in cross section in FIG. 3 can define multiple lumens (and is also referred to herein as a "multilumen tube"). In some implementations, the multilumen tube 58 forms a central or inner portion of the lead body 52 and extends from a proximal portion to a distal portion of the body 52. As shown, in some embodiments, the multilumen tube 58 has four lumens 60, 62, 64, 66. In other embodiments, the multilumen tube 58 has a single lumen, two or more lumens, three or more lumens, four or more lumens, or any other suitable number of lumens. Further, in some embodiments one or more of the lumens are offset from the longitudinal axis of the multilumen tube 58. For example, the first lumen 60 has a longitudinal axis that is non-coaxial with respect to the longitudinal axis of the multilumen tube 58.

As mentioned above, in some embodiments the lumens 60, 62, 64, 66 provide a passageway through which conductors can pass and electrically connect one or more of electrodes 46, 48, 50 to the connector 54. The conductors utilized may take on any configuration providing the necessary functionality. For example, as will be appreciated, the conductors coupling the electrodes 48 and/or 50 to the connector 54 (and thus, to the pulse generator 12) may be coiled conductors defining an internal lumen for receiving a stylet or guidewire for lead delivery. Lumen 66, for example, could receive a coiled conductor defining an internal lumen. Conversely, in various embodiments, the conductor to the high voltage electrode 46 may be a multi-strand cable conductor.

Surprisingly, certain lead body configurations as set forth in certain embodiments herein can reduce or minimize conductor flex fatigue and, in some cases, failure. That is, specific characteristics of the lead body can be optimized to reduce the changes of one or more of the conductors disposed within the lead body lumens will be damaged or severed as a result of bending or flexing the lead body.

Figure 4A:
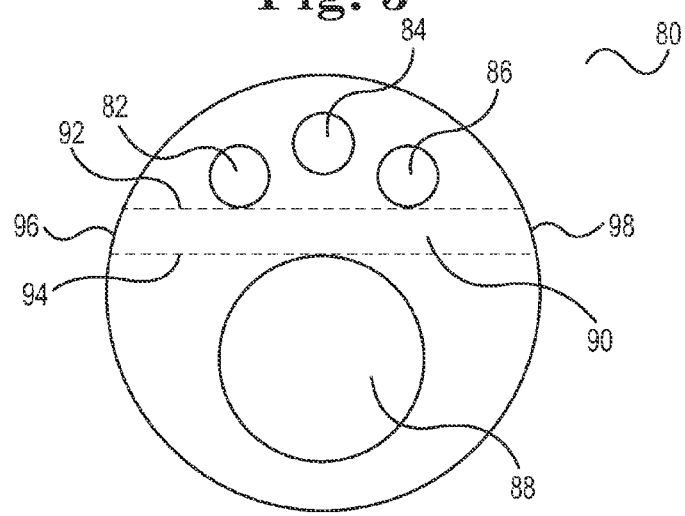
FIG. 4A is a schematic cross-section drawing of a portion of a lead, according to another embodiment.
Figure 4B:
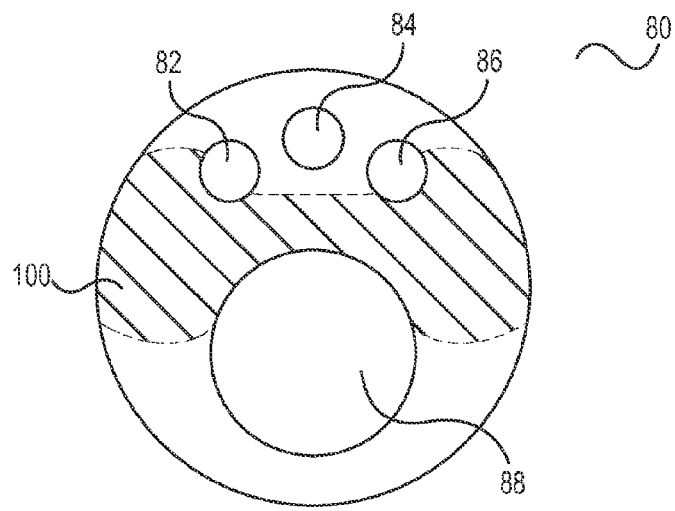
FIG. 4B is a schematic cross-section drawing of the portion of the lead of FIG. 4A.

One example of such a lead body configuration is set forth, according to one embodiment, in FIGS. 4A and 4B. FIGS. 4A and 4B depict a lead body 80 having three smaller lumens 82, 84, 86 and a larger lumen 88. In one implementation, the smaller lumens 82, 84, 86 are configured to receive cable conductors while the larger lumen 88 is configured to receive a coiled conductor. In a further alternative, any of the lumens 82, 84, 86, 88 can receive any known type of conductor.

According to one embodiment, the lead body 80 configuration forms a support portion 90 as best shown in FIG. 4A. The support portion 90, which is also referred to herein as a "support member," "support component," "support beam," and "beam," is a portion of the lead body that is defined, at a minimum, as the portion of the lead body "framed" by the two smaller lumens 82, 86, the larger lumen 88, and the two sides 96, 98 defined by the outer wall of the lead body 80. More specifically, it is best to imagine the support component 90 as a beam 90 having an "upper" border 92 defined in part by the walls of the lumens 82 and 86, a "lower" border 94 defined in part by the wall of the lumen 88, and the two sides 96 and 98 defined by the outer walls of the lead body 80. The distance between the upper border 92 and lower border 94 will also be referred to herein as "thickness," and the distance between the two sides 96, 98 will also be referred to herein as "width." It is understood that "upper" and "lower" as used herein are simply used to identify portions of the figures and are not intended to identify any component as being above or below the other or otherwise limit the configuration of the beam to a specific embodiment.

Alternatively, the body 80 configuration forms a structural support identified as the full shaded area 100 in FIG. 4B, which includes the area identified as the beam or support portion 90 in FIG. 4A. That is, in addition to the support portion 90, an additional region of the lead body which shall be referred to herein as the support region 100 may also provide additional structural support—in combination with the support beam 90—to reduce conductor flex fatigue. That is, in some embodiments, maintaining the entire support region 100 as a solid component that does not include any lumens or other types of apertures or cavities optimizes the minimization of conductor flex fatigue and/or failure.

It is understood that the support beam 90 and the support region 100 do not need to be made of a different material in comparison to the rest of the lead body 80. To the contrary, one advantage of this new lead body configuration is that no new material needs to be added to the lead body 80. Instead, simply positioning the lumens 82, 84, 86, 88 of the body 90 to form the support beam 90 and/or the support region 100 is sufficient to minimize flex fatigue in those conductors positioned in the lumens 82, 84, 86, 88.

In contrast to the lead body 80 embodiments with the support beam 90 and/or the support region 100 as shown in FIGS. 4A and 4B, it was found that known lead body configurations, such as the lead body 58 configuration of FIG. 3 for example, can become deformed as a result of bending or flexing the body. More specifically, one or more of the lumens 60, 62, 64, 66 can become deformed as a result of the flexing, often resulting in one or more of the lumens having an inner diameter ("I.D.") in the deformed portion of the lead body 58 that is less than the outer diameter ("O.D.") of a conductor disposed within the lumen. During flexing or bending, the deformation and resulting reduced I.D. of the lumen can apply damaging radial forces on the conductor while also restricting the natural axial movement of the conductor during such flexing or bending, thereby applying potentially damaging axial forces as well. After repeated flexing or bending, this deformation can result in the conductor suffering flexural fatigue (also referred to as "flex fatigue"), and in some cases, failure. "Flexural fatigue" is intended for purposes of this application to mean the fraying, severing, stressing, or any other type of damage to a conductor caused by fatigue as a result of repeated flexing or bending of the conductor, including failure of the conductor as a result of this fatigue. In addition, "flexural fatigue failure" and "flex fatigue failure" is intended to mean specifically the severing or physical disconnection of the conductor as a result of flexural fatigue. Further, any reference to "reducing flexural fatigue" or "flexural fatigue reduction" is intended to mean a reduction or minimization of any fraying, severing, stressing, or any other type of damage caused by fatigue as a result of repeated flexing or bending of the conductor and further means any enhancement or increase in the resistance to or reduction of such damage.

Unlike the prior art lead body configurations such as that shown in FIG. 3, the embodiments as depicted in FIGS. 4A and 4B with the support beam 90 and/or the support region 100 provide structural support to the lead body 80 while the body 80 is being bent or flexed that reduces or eliminates the permanent deformation of the lumens 82, 84, 86, 88, thereby reducing the risk of flex fatigue of any of the conductors disposed in those lumens 82, 84, 86, 88. That is, a lead body having the configuration of the lead body 80 of FIGS. 4A and/or 4B reduces conductor flex fatigue.

In one embodiment in which the lead body 80 has a diameter of around 0.0678 inches, the support beam 90 has a thickness of at least 0.0015 inches. Alternatively, in various embodiments in which the lead body 80 has a diameter of 0.0678 inches or more, the support beam 90 has a thickness of at least 2.24% of the total lead body diameter. In further embodiments, the thickness of the support beam can vary depending on the lead body material and other variable characteristics of the lead body.

Without being limited by theory, it is speculated that the support beam 90 and/or the support region 100 provide support that reduces conductor flex fatigue because the beam 90 and/or region 100 reduce the damage caused by the compression forces on the internal portions of the lead body. More specifically, when a lead body is bent or flexed, the outer edge of the lead body at the top of the bend is urged downward such that the outer edge at the top of the bend creates a downward compressive force on the body. At the same time, the outer edge of the lead body at the bottom of the bend is urged upward such that the edge creates an upward compressive force on the body. The end result is that the internal components of the lead body are being compressed by these opposing forces. It is theorized that the support beam 90 and/or support region 100 provide support across the lead body to resist the compressive forces, thereby reducing the deformation of the lumens 82, 84, 86, 88.

Figure 5A:
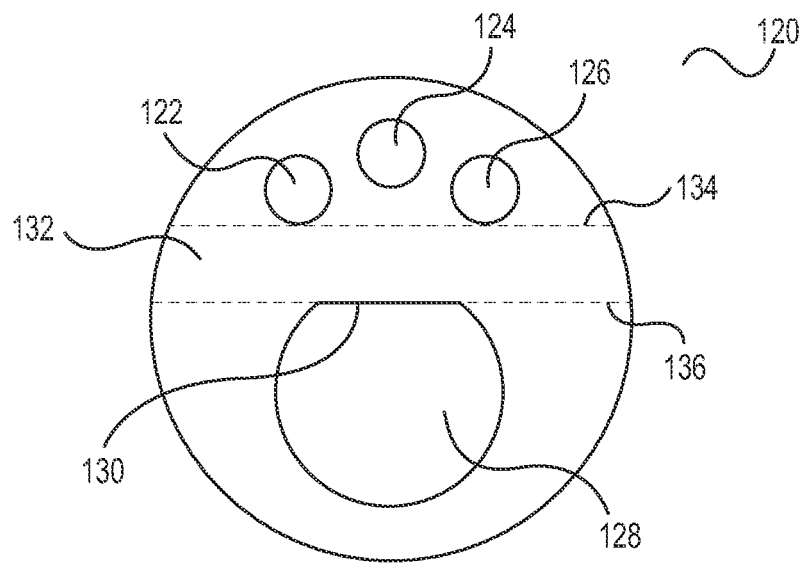
FIG. 5A is a schematic cross-section drawing of a portion of a lead, according to a further embodiment.
Figure 5B:
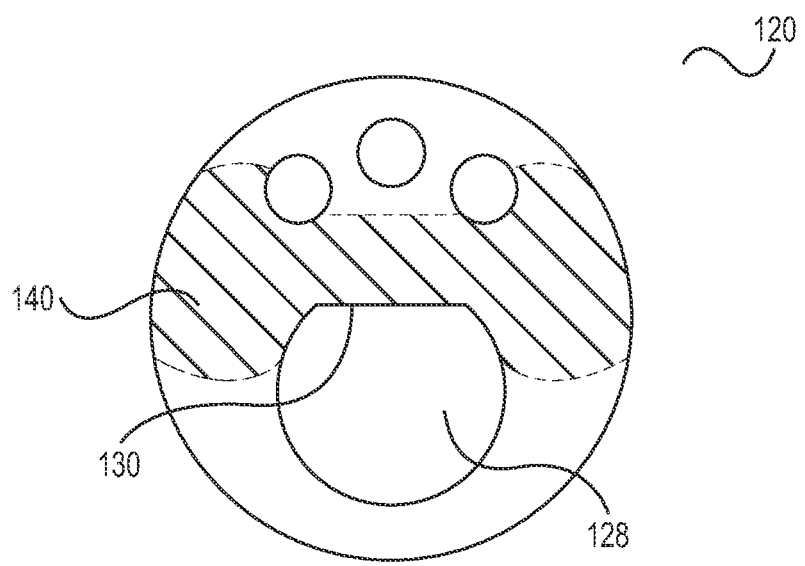
FIG. 5B is a schematic cross-section drawing of the portion of the lead of FIG. 5A.

A further implementation is shown in FIGS. 5A and 5B, which depict a lead body 120 having three smaller lumens 122, 124, 126 and a larger lumen 128. In this embodiment, the larger lumen 128 has a generally circular circumference except for a semi-straight portion 130 along a portion of the circumference closest to the three smaller lumens 122, 124, 126 (also referred to as an "upper" portion of the circumference). The term "semi-straight portion" as used herein is intended to mean any portion of the circumference of a lumen that has a curvature that is less than the curvature of the remainder of the circumference. Thus, the semi-straight portion 130 can have a curvature, so long as it is less than the curvature of the remainder of the circumference of the lumen.

As with the embodiment in FIG. 4A, the lead body 120 configuration in FIG. 5A forms a support component 132. The semi-straight portion 130 in this embodiment is disposed along the circumference of the lumen 128 and is substantially adjacent to or defines one edge of the support component 132. The thickness between the upper border 134 and the lower border 136 is optimized because of the semi-straight portion 130. That is, the replacement of a standard lumen having a substantially circular cross-section with a lumen having the semi-straight portion 130 results in a thicker support beam 132 than an equivalent body with a circular large lumen. This thicker support beam 132 results in further optimization or enhancement of the reduction in conductor flex fatigue.

The body 120 as shown in FIG. 5B can also form a support region 140 as identified by the full shaded area 140. As with the support beam 132 in FIG. 5A, the semi-straight portion 130 expands the volume of the support region in comparison to a lead body with a standard circular large lumen, thereby enhancing or optimizing the reduction in conductor flex fatigue.

Figure 6A:
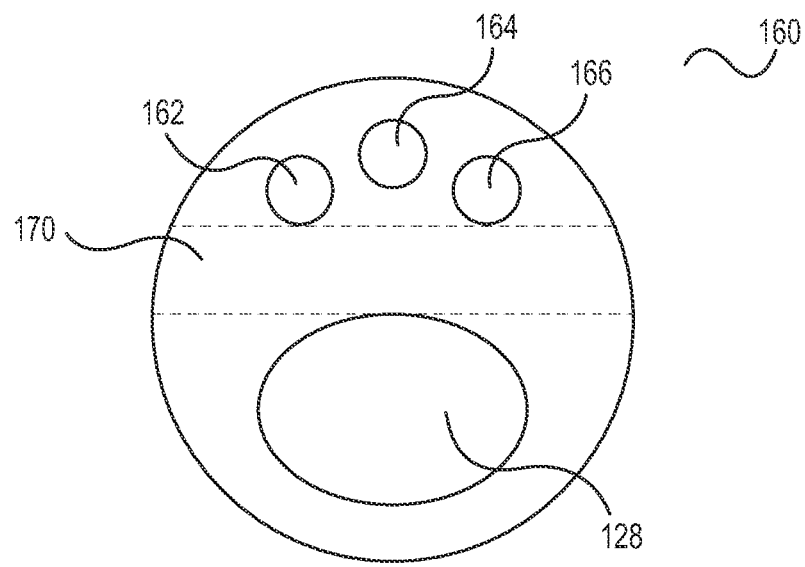
FIG. 6A is a schematic cross-section drawing of a portion of a lead, according to yet another embodiment.
Figure 6B:
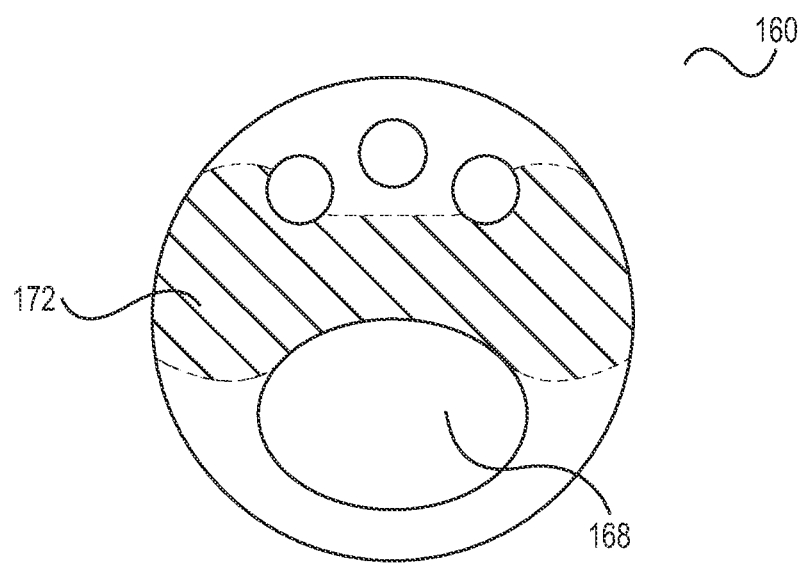
FIG. 6B is a schematic cross-section drawing of the portion of the lead of FIG. 6A.

A further implementation is shown in FIGS. 6A and 6B, which depict a lead body 160 having three smaller lumens 162, 164, 166 and a larger lumen 168. In this embodiment, the larger lumen 168 has a substantially elliptical cross-section. Like the semi-straight portion described above, the substantially elliptical cross-section results in a thicker support beam 170 in comparison to a standard circular larger lumen. That is, the upper edge of the substantially elliptical lumen 168 is not as close to the three smaller lumens 162, 164, 166 as the upper edge of a substantially circular lumen would be. Thus, the substantially elliptical lumen 168 enhances or optimizes the reduction in conductor flex fatigue.

The body 160 as shown in FIG. 6B can also form a support region 172 as identified by the full shaded area 172. As with the support beam 170 in FIG. 6A, the substantially elliptical lumen 168 expands the volume of the support region 172 in comparison to a lead body with a standard circular large lumen, thereby enhancing or optimizing the reduction in conductor flex fatigue.

Figures 7A, 7B, 7C:
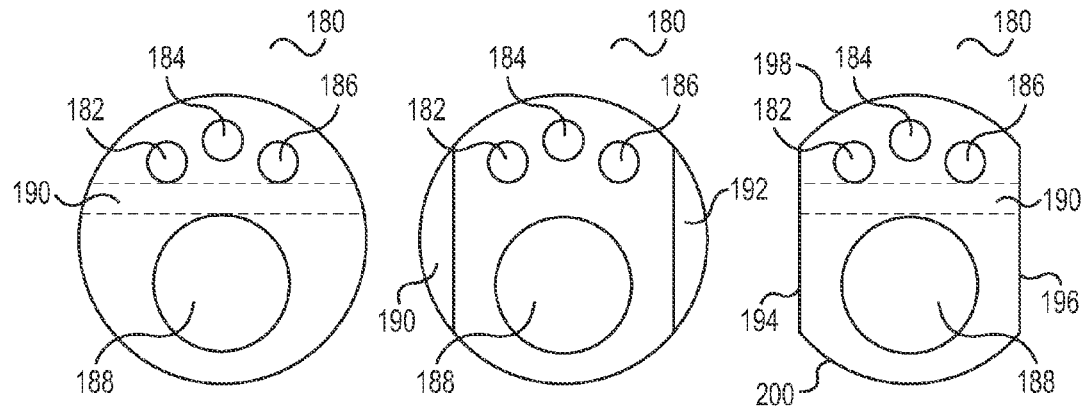
FIG. 7A is a schematic cross-section drawing of a portion of a lead, according to a further embodiment.
FIG. 7B is a schematic cross-section drawing of the portion of the lead of FIG. 7A.
FIG. 7C is a schematic cross-section drawing of the portion of the lead of FIG. 7A in which the lead body has been altered.

A further implementation is shown in FIG. 7C, which depicts a lead body 180 having three smaller lumens 182, 184, 186, a larger lumen 188, and two semi-straight sides 194, 196. As shown in FIGS. 7A and 7B, the body 180 having two semi-straight sides 194, 196 can be formed by starting with a substantially circular body 180 (as shown in FIG. 7A) similar to the lead body 80 of FIG. 4A. The lead body 180 is then altered by removing the side portions 190, 192 shown in FIG. 7B. Alternatively, the lead body 180 can be formed or otherwise created with the semi-straight sides 194, 196, rather than removing the side portions to create those sides 194, 196.

It is understood that the semi-straight sides 194, 196 need not be straight. In fact, "semi-straight sides" is intended for purposes of this application to mean any side of a lead body that has less curvature than the remaining circumference of the body. Thus, in FIG. 7C, the sides 194, 196 need only have less curvature than the curved portions 198, 200.

While the configuration of the lead body 180 in FIG. 7C does not result in a thicker support beam 190 in comparison to other configurations, the configuration does result in enhance or optimized reduction in conductor flex fatigue. Without being limited by theory, it is speculated that the enhancement or optimization results from the semi-straight sides 194, 196. As discussed above, the compressive forces created by the bending of the lead body 180 place strain on the internal components of the lead body 180. It is believed that those compressive forces are exacerbated by the side portions 190, 192, which result in a larger cross-sectional lead body area and thus more material that must stretch to counteract the bending. By removing the side portions 190, 192, there is less material that must stretch and the amount of the compressive forces is reduced.

Regardless of the theory, according to one embodiment, the semi-straight sides 194, 196 as shown in FIG. 7C reduce conductor flex fatigue.

Figure 8A:
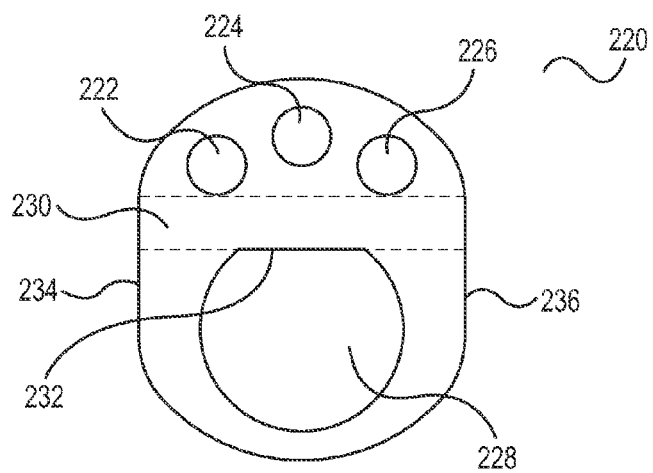
FIG. 8A is a schematic cross-section drawing of a portion of a lead, according to another embodiment.
Figure 8B:
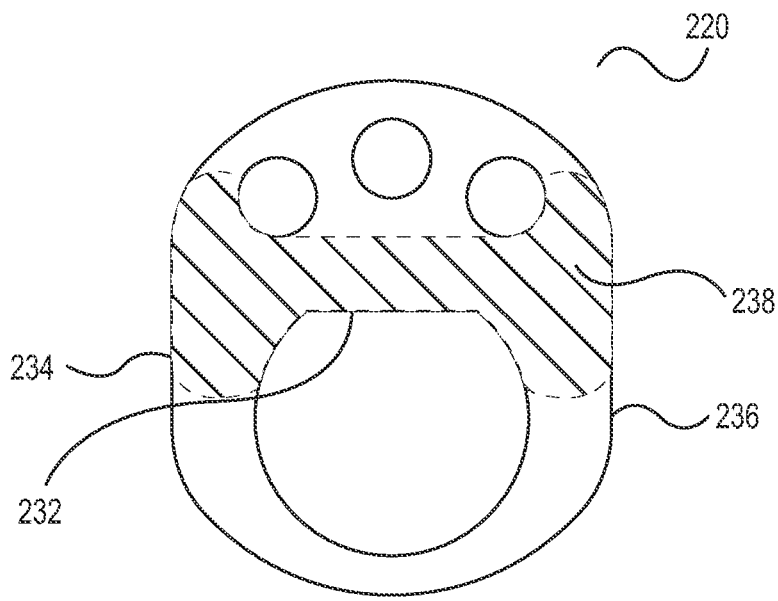
FIG. 8B is a schematic cross-section drawing of the portion of the lead of FIG. 8A.

Yet another embodiment is shown in FIGS. 8A and 8B, which depict a lead body 220 having three smaller lumens 222, 224, 226, a larger lumen 228, a semi-straight portion 232, and two semi-straight sides 234, 236. The configuration of the lead body 220 also forms a support beam 230. The semi-straight portion 232 results in a thicker support beam 230 in comparison to a standard circular larger lumen. Thus, the semi-straight portion 232 and the two semi-straight sides 234, 236 enhance or optimize the reduction in conductor flex fatigue.

The body 220 as shown in FIG. 8B can also form a support region 238 as identified by the full shaded area 238. As with the support beam 230 in FIG. 8A, the semi-straight portion 232 and the two semi-straight sides 234, 236 enhance or optimize the reduction in conductor flex fatigue.

EXAMPLES

The impact of flexing certain lead body configurations multiple times was examined. More specifically, three-dimensional computer modeling was used to perform a finite element analysis on various lead body configurations and the resulting deformations were examined. All the specifications of various lead body configurations—including material properties, dimensions, etc—were entered into a software program and then the program modeled the lead body configurations being subjected to the forces associated with the bending of the lead body multiple times. The results provided by the software program were in the form of an image that predicted the amount of deformation of the lead body, including deformation of the lumens that would result in damage to the conductors disposed in those lumens.

Example 1

Figure 9:
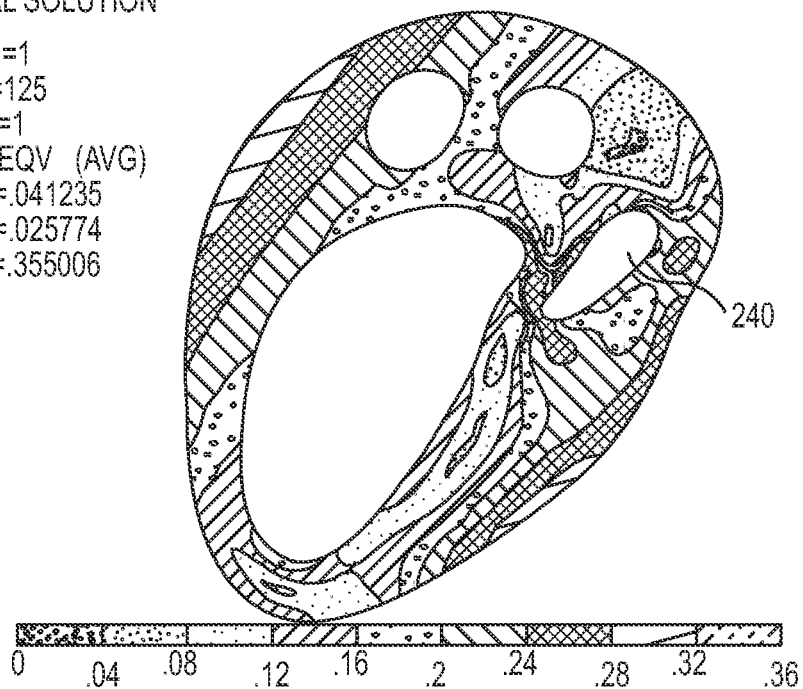
FIG. 9 is a computer modeled image of the projected deformation of the lead body depicted in FIG. 3 caused by flexural fatigue.

In this example, the lead body configuration that was examined was the lead body configuration depicted in FIG. 3. The software projected deformation as shown in FIG. 9, including significant deformation of lumen 240 that would result in damage to any conductor disposed within the lumen 240.

Example 2

Figure 10A:
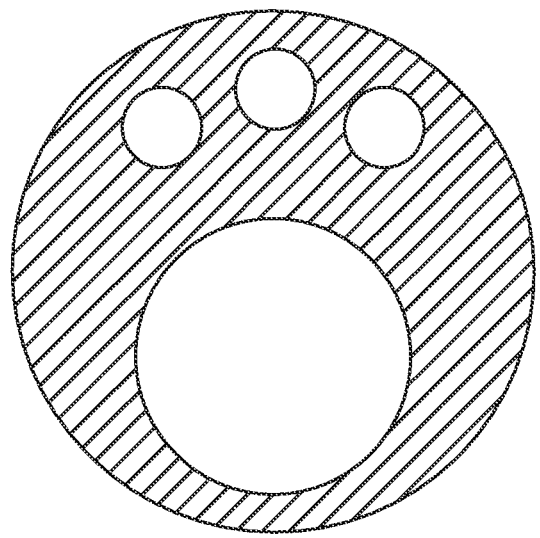
FIG. 10A is a computer modeled image of a lead body being examined for flexural fatigue, according to one embodiment.
Figure 10B:
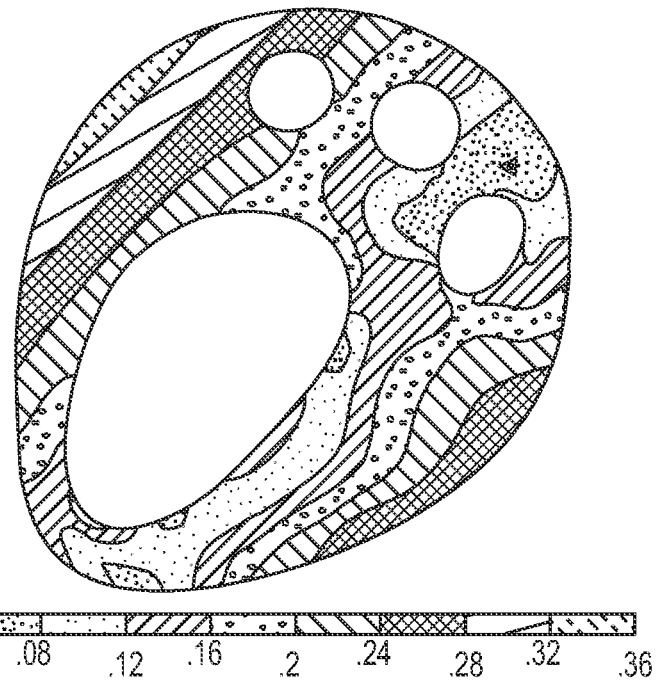
FIG. 10B is a computer modeled image of the projected deformation of the lead body depicted in FIG. 10A caused by flexural fatigue.

In this example, the lead body configuration that was examined is set forth in FIG. 10A. This configuration is similar to the lead body in depicted in FIGS. 4A and 4B. The software projected deformation as shown in FIG. 10B, which does not exhibit significant deformation.

Example 3

Figure 11A:
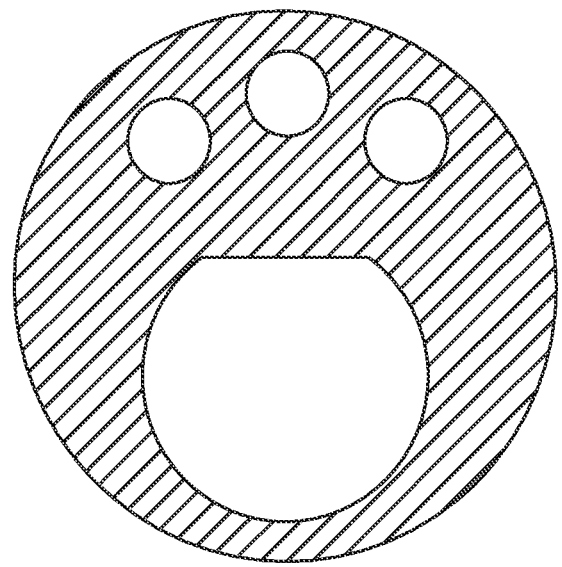
FIG. 11A is a computer modeled image of a lead body being examined for flexural fatigue, according to one embodiment.
Figure 11B:
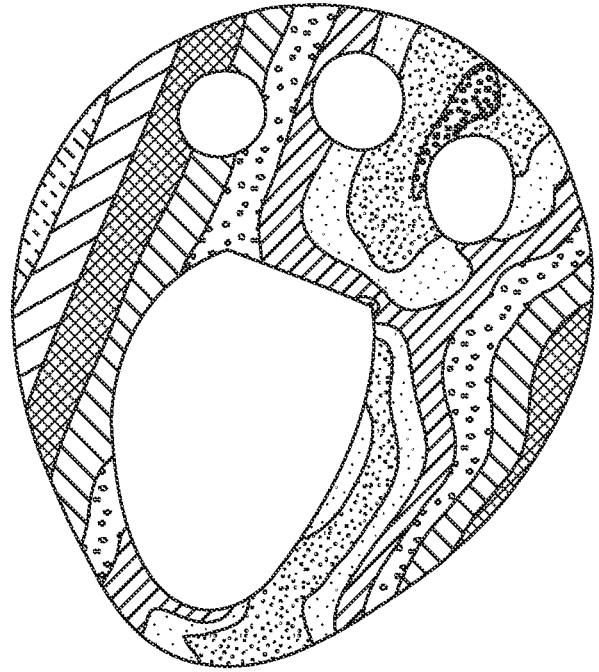
FIG. 11B is a computer modeled image of the projected deformation of the lead body depicted in FIG. 11A caused by flexural fatigue.

In this example, the lead body configuration that was examined is set forth in FIG. 11A. This configuration is similar to the lead body depicted in FIGS. 5A and 5B. The software projected deformation as shown in FIG. 11B, which does not exhibit significant deformation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical lead comprising a lead body formed from a polymeric material, the lead body comprising:
    a coil lumen defined by the polymeric material of the lead body, the coil lumen extending from a proximal portion to a distal portion of the lead body, the coil lumen defined by a coil lumen wall;
    three cable lumens defined by the polymeric material of the lead body, the three cable lumens comprising a middle cable lumen, a left cable lumen located to the left of the middle cable lumen, and a right cable lumen located to the right of the middle cable lumen, each of the three cable lumens extending from the proximal portion to the distal portion, each of the three cable lumens defined by a respective cable lumen wall, each of the three cable lumens smaller in diameter than the coil lumen; and
a support portion formed from the polymeric material of the lead body, the support portion extending longitudinally within the lead body and disposed between the coil lumen and the three cable lumens, the support portion comprising a beam formed from the polymeric material of the lead body, the beam comprising:
an upper border defined in part by the cable lumen walls of the right cable lumen and the left cable lumen, the upper border extending straight from the cable lumen wall of the right cable lumen to the cable lumen wall of the left cable lumen, the upper border located below and remote from the cable lumen wall of the middle cable lumen;
a lower border defined in part by the coil lumen wall;
a first lateral side defining a first exterior surface of the medical lead; and
a second lateral side opposite the first lateral side, the second lateral side defining a second exterior surface of the medical lead,
wherein the beam has a minimum thickness defined by the upper border and the lower border, the beam has a width extending from the first lateral side of the lead body to the second lateral side, and the minimum thickness is configured to reduce flexural fatigue of a conductor disposed within any of the coil lumen and the three cable lumens.

2. The medical lead of claim 1, wherein the minimum thickness is maintained from the first lateral side to the second lateral side.

3. The medical lead of claim 2, wherein the minimum thickness is at least 2.24% of a total diameter of the lead body.

4. The medical lead of claim 2, wherein the minimum thickness is at least 0.0015 inches.

5. The medical lead of claim 1, wherein the coil lumen wall has a circumference, wherein the circumference has a semi-straight portion, wherein the semi-straight portion is substantially adjacent to the support portion and is substantially parallel with the width of the beam, wherein the semi-straight portion is configured to further reduce the flexural fatigue.

6. The medical lead of claim 1, wherein each of the first and second lateral sides of the lead body comprise a semi-straight side extending longitudinally along each of the first and second lateral sides, wherein each of the semi-straight sides are configured to further reduce the flexural fatigue.

7. The medical lead of claim 1, wherein the coil lumen has a substantially elliptical cross-section, wherein the substantially elliptical cross-section is configured to further reduce the flexural fatigue.

8. The medical lead of claim 1, wherein at least a portion of the proximal portion comprises polyurethane.

9. The medical lead of claim 1, wherein the polymeric material is polyurethane.

10. The medical lead of claim 1, wherein the diameters of the three cable lumens are equal to each other.

11. The medical lead of claim 1, wherein each of the upper border and the lower border extends straight across the lead body from the first lateral side to the second lateral side.

12. A medical lead comprising a lead body formed from a polymeric material and having a cross-section, the cross-section comprising:
a coil lumen defined by the polymeric material of the lead body, the coil lumen configured to receive a coil conductor, the coil lumen defined by a coil lumen wall;
three cable lumens defined by the polymeric material of the lead body, the three cable lumens comprising a middle cable lumen, a left cable lumen located to the left of the middle cable lumen, and a right cable lumen located to the right of the middle cable lumen, the middle cable lumen located above the right cable lumen and the left cable lumen, each of the three cable lumens configured to receive a respective cable conductor, each of the three cable lumens defined by a respective cable lumen wall, each of the three cable lumens smaller in diameter than the coil lumen; and
a support portion defined in the lead body and disposed between the coil lumen and the three cable lumens to separate the coil lumen from the three cable lumens, the support portion comprising a beam formed by the polymeric material, the beam comprising:
an upper border defined in part by the cable lumen walls of the right cable lumen and the left cable lumen, the upper border extending from the cable lumen wall of the right cable lumen to the cable lumen wall of the left cable lumen, the upper border located below the cable lumen wall of the middle cable lumen;
a lower border defined in part by the coil lumen wall;
a first lateral side defining a first exterior surface of the medical lead; and
a second lateral side opposite the first lateral side, the second lateral side defining a second exterior surface of the medical lead,
wherein the beam has a minimum thickness defined by the upper border and the lower border, the beam has a width extending from the first lateral side of the cross-section to the second lateral side, the minimum thickness is at least 2.24% of a total diameter of the lead body, and the minimum thickness is configured to reduce flexural fatigue of the coil conductor or the cable conductors.

13. The medical lead of claim 12, wherein the coil lumen wall has a circumference, wherein the circumference has a semi-straight portion, wherein the semi-straight portion is substantially adjacent to the support portion and is substantially parallel with the width of the support portion, wherein the semi-straight portion is configured to further reduce the flexural fatigue.

14. The medical lead of claim 12, wherein each of the first and second lateral sides of the lead body comprise a semi-straight side extending longitudinally along each of the first and second lateral sides, wherein each of the semi-straight sides are configured to further reduce the flexural fatigue.

15. The medical lead of claim 12, wherein the coil lumen has a substantially elliptical cross-section, wherein the substantially elliptical cross-section is configured to further reduce the flexural fatigue.

16. The medical lead of claim 12, wherein the minimum thickness is at least 0.0015 inches.

17. The medical lead of claim 12, wherein the polymeric material is polyurethane.

18. The medical lead of claim 12, wherein the diameters of the three cable lumens are equal to each other.

19. The medical lead of claim 12, wherein each of the upper border and the lower border extends straight across the lead body from the first lateral side to the second lateral side.

20. A medical lead comprising a lead body formed from polyurethane and having a cross-section, the cross-section comprising:
a coil lumen having a coil lumen wall defined by the polyurethane of the lead body;
three cable lumens each having a respective cable lumen wall defined by the polyurethane of the lead body, the three cable lumens comprising a middle cable lumen, a left cable lumen located to the left of the middle cable lumen, and a right cable lumen located to the right of the middle cable lumen, the middle cable lumen located above the right cable lumen and the left cable lumen, each of the three cable lumens smaller in diameter than the coil lumen; and a beam formed by the polyurethane of the lead body and disposed between the coil lumen and the three cable lumens to separate the coil lumen from the three cable lumens, the beam comprising:

an upper border defined in part by the cable lumen walls of the right cable lumen and the left cable lumen, the upper border extending from the cable lumen wall of the right cable lumen to the cable lumen wall of the left cable lumen, the upper border located below the cable lumen wall of the middle cable lumen;

a lower border defined in part by the coil lumen wall;

a first lateral side defining a first exterior surface of the medical lead; and a second lateral side opposite the first lateral side, the second lateral side defining a second exterior surface of the medical lead, wherein the beam has a minimum thickness of at least 0.0015 inches measured between the upper border and the lower border, the minimum thickness is maintained from the first lateral side to the second lateral side, and the minimum thickness is configured to reduce flexural fatigue within the lead body.

* * * * *